(12) United States Patent
Geisen et al.

(10) Patent No.: US 6,604,926 B2
(45) Date of Patent: Aug. 12, 2003

(54) APPARATUS FOR PRODUCING ABSORBENT PADS FROM A FLOCK-AIR MIXTURE

(75) Inventors: Armin Geisen, Melsbach (DE); Ulrich Mertgen, Meinborn (DE); Sascha Haase, Neuwied (DE)

(73) Assignee: Winkler + Dünnebier Aktiengesellschaft (DE)

(*) Notice: Subject to any disclaimer, the term of this patent is extended or adjusted under 35 U.S.C. 154(b) by 0 days.

(21) Appl. No.: 09/852,289

(22) Filed: May 9, 2001

(65) Prior Publication Data

US 2002/0003316 A1 Jan. 10, 2002

(30) Foreign Application Priority Data

May 9, 2000 (DE) .......................................... 100 22 500

(51) Int. Cl.$^7$ ................................................. B27N 3/04
(52) U.S. Cl. .................... 425/81.1; 425/80.1; 425/83.1; 425/115; 425/120; 425/130; 264/113; 264/121
(58) Field of Search ................................ 425/80.1, 81.1, 425/83.1, 115, 120, 121, 130, 363; 264/112, 113, 121; 19/304, 308

(56) References Cited

U.S. PATENT DOCUMENTS

| | | | |
|---|---|---|---|
| 4,383,349 A | | 5/1983 | Marshall .................... 19/0.56 |
| 4,908,175 A | | 3/1990 | Angstadt .................... 264/113 |
| 4,927,346 A | | 5/1990 | Kaiser et al. ............... 425/81.1 |
| 5,004,579 A | * | 4/1991 | Wislinski et al. ........... 264/112 |
| 5,044,052 A | | 9/1991 | Hertel et al. ................. 28/105 |
| 5,064,484 A | | 11/1991 | Craig et al. ................ 156/62.6 |
| 5,097,574 A | * | 3/1992 | Hertel et al. .................. 19/308 |
| 5,245,728 A | * | 9/1993 | Rupp et al. .................... 19/148 |
| 5,885,623 A | * | 3/1999 | Edvardsson et al. .......... 19/302 |
| 6,033,199 A | | 3/2000 | Vonderhaar et al. ........ 425/81.1 |
| 6,416,697 B1 | * | 7/2002 | Venturino et al. ........... 264/113 |

FOREIGN PATENT DOCUMENTS

| | | |
|---|---|---|
| DE | 33 42963 A1 | 6/1985 |
| DE | 34 13925 A1 | 10/1985 |
| DE | 34 15196 A1 | 10/1985 |
| DE | 36 14969 C2 | 11/1986 |
| DE | 37 36275 A1 | 5/1989 |
| DE | 41 17 252 A1 | 12/1992 |
| DE | 43 19 445 A1 | 12/1994 |
| DE | 43 35 919 A1 | 4/1995 |
| DE | 197 06 404 A1 | 8/1998 |
| DE | 198 23 954 A1 | 12/1999 |
| EP | 0 627 211 A1 | 12/1994 |
| FR | 2 690 843 | 11/1993 |
| GB | 2 191 515 A | 12/1987 |
| GB | 2 191 794 A | 12/1987 |
| GB | 2 294 703 A | 5/1996 |
| WO | WO 95/10994 | 4/1995 |
| WO | WO 96/07792 | 3/1996 |

OTHER PUBLICATIONS

Patent Abstracts of Japan, Publication No. 62231032, Publication date Oct. 09, 1987, 1 page.

European Search Report dated Aug. 17, 2001, 4 pages.

* cited by examiner

*Primary Examiner*—James P. Mackey
*Assistant Examiner*—Donald Heckenberg
(74) *Attorney, Agent, or Firm*—Rosenthal & Osha L.L.P.

(57) ABSTRACT

In an apparatus for and method of producing absorbent pads from a flock-air mixture which is fed through a feed conduit to a shaping recess carrier to form the respective absorbent pad, the carrier rotates or circulates in a predetermined direction of operation. For excess air in the region of the flock-laying device is to be sucked away in a simple fashion without adversely affecting the process of shaping the absorbent pad, the feed conduit feeding the flock-air mixture to the carrier is branched into at least first and second conduits, the first conduit carrying a first partial flow of the mixture and the second conduit carrying a second partial flow thereof. The first and second conduits are directed on to the carrier in such a way that the second partial flow meets the carrier substantially downstream of the first partial flow in the direction of operation of the carrier.

9 Claims, 3 Drawing Sheets

APPARATUS FOR PRODUCING ABSORBENT PADS FROM A FLOCK-AIR MIXTURE

FIELD OF THE INVENTION

Figure 1:
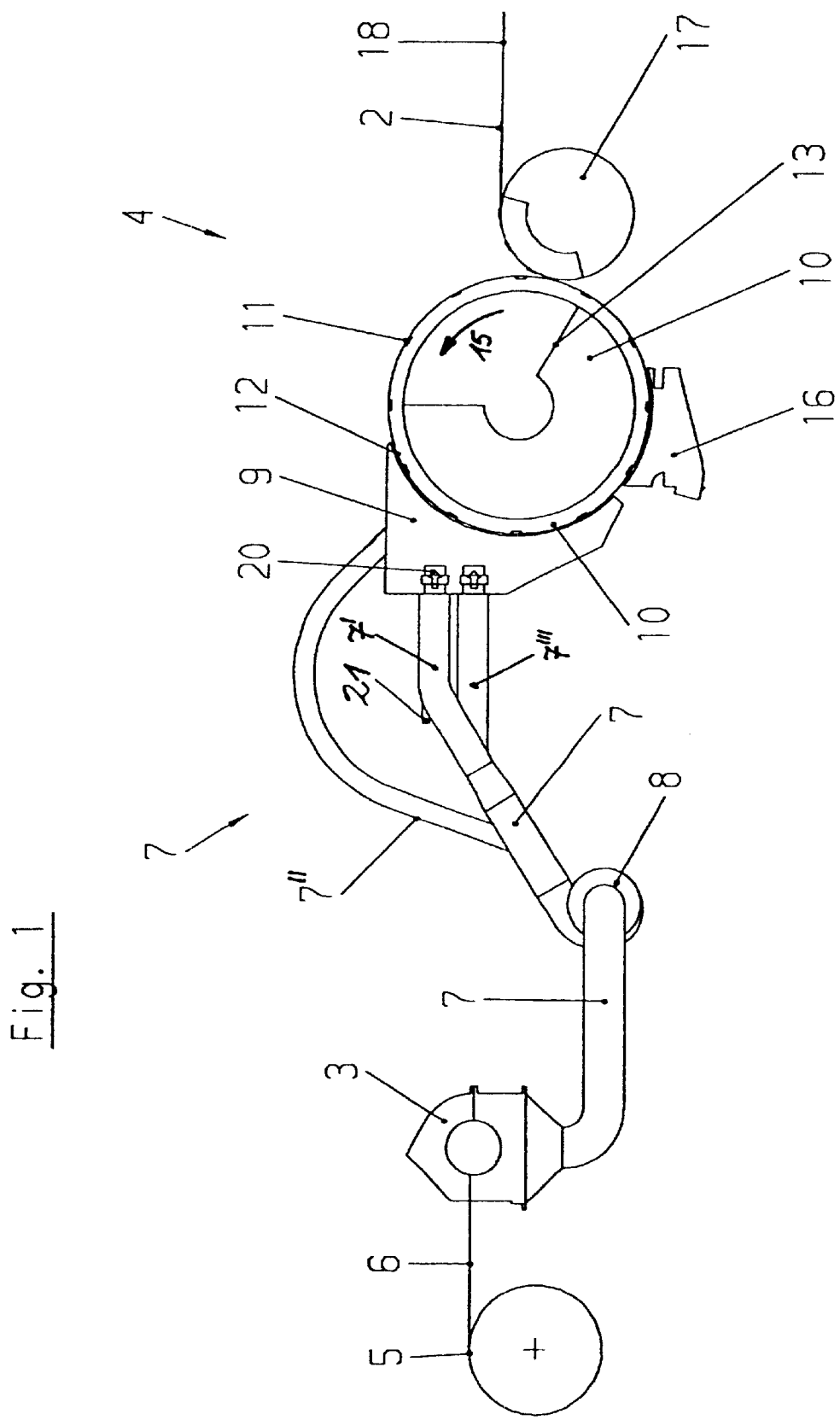

The present invention concerns an apparatus and a method of producing absorbent pads from a flock-air mixture.

BACKGROUND OF THE INVENTION

In the case of machines for producing absorbent pads as for sanitary napkins, panty liners, disposable diapers or the like, the usual practice is for an absorbent pad or flock core to be formed from a hydrophilic flock mixture on a flock-laying device. The flocks which are required for that purpose are fed to the flock-laying device in the form of a flock-air mixture, being supplied thereto from a disintegrating or pulping device, through a feed conduit.

As the disintegrating device or grinding device converts large amounts of mechanical energy into heat energy while it is in operation, it suffers from a substantial rise in temperature. That fact requires a carrier air flow which is as large as possible from the disintegrating device, to convey the flock-air mixture, whereby that air flow produces the desired effect of dissipating heat from the disintegrating device, and thus affords a cooling action therefor. The comparatively great carrier air flow however entails the disadvantage in the region of the flock-laying device that excessively large amounts of air occur there, and cannot be sufficiently rapidly sucked away by the suction box of the flock-laying device, so that they adversely affect the procedure involved in shaping the suction pads from the flock-air mixture in the flock-laying device.

SUMMARY OF THE INVENTION

An object of the present invention is to provide an apparatus for producing absorbent pads from a flock-air mixture in which any excess air in the region of formation of the absorbent pads can be easily removed by a suction effect without adversely affecting the procedure involved in shaping the absorbent pads.

Another object of the present invention is to provide an apparatus for producing absorbent pads from a feed of flock-air mixture through a feed conduit, which provides for a controlled feed of the flock-air mixture to locations in which the respective absorbent pads are formed, thereby enhancing the efficiency of the apparatus.

Still another object of the present invention is to provide a method of producing absorbent pads from a flock-air mixture, which can control a feed of the mixture in such a way as to afford a simple but efficient operating procedure in terms of shaping absorbent pads.

In accordance with the principles of the present invention in the apparatus aspect the foregoing and other objects are attained by an apparatus for producing absorbent pads from a flock-air mixture which is fed through a feed conduit to a shaping recess carrier for forming the respective absorbent pads. The shaping recess carrier rotates in a predetermined direction or circulates in a predetermined circulatory direction. The feed conduit which carries the flow of flock-air mixture has a branching to provide at least first and second conduits. The first conduit is operable to carry a first partial flow of the flock-air mixture and the second conduit is operable to carry a second partial flow of the flock-air mixture. The first and second conduits are directed on to the shaping recess carrier in such positions that the second partial flow through the second conduit meets the shaping recess carrier substantially downstream of the first partial flow through the first conduit in the direction of operating movement of the shaping recess carrier.

Further in accordance with the invention in the method aspect the foregoing and other objects are attained by a method of producing absorbent pads from a flock-air mixture which is fed through a feed conduit to a shaping recess carrier for forming the respective absorbent pads, the carrier rotating in a predetermined direction of rotation or circulating in a predetermined circulatory direction. The flock-air mixture is divided into at least first and second partial flows, the second thereof being directed on to the shaping recess carrier at such a position that it meets the carrier substantially downstream of the first partial flow in the direction of operation of the shaping recess carrier.

It will be noted at this point that the above-mentioned component referred to as the shaping recess carrier may involve for example a rotatable flock-shaping wheel or an endless flock-shaping belt which circulates around guide rollers or a corresponding flock-shaping chain.

The shaping recess carrier is generally a component part of a flock-laying device which, as a further essential component thereof, includes a hollow flock box, with the shaping recess carrier being movable relative to the flock box. In accordance with the invention, at least first and second conduits open into the flock box, each of the conduits carrying a respective partial flow of the flock-air mixture and feeding it to the shaping recess carrier.

The movement of the shaping recess carrier with respect to the flock box means that shaping recesses continuously move into that region in space which is supplied with flock-air mixture from the flock box. The shaping recesses in the shaping recess carrier are initially not yet or scarcely filled with flock so that the sieve-like bottoms of such recesses still involve a comparatively high degree of permeability to the air. It is precisely that fact that the present invention puts to good use insofar as it provides for passing one of the first and second partial flows of the divided flock-air mixture into that region of the flock box in which there are disposed shaping recesses which are filled with flock to an only slight degree and which thus have a sieve-like bottom which still affords good permeability to the air. In that way the suction device of the flock-laying device which sucks the air away from the flock-air mixture to cause flock to be deposited in the respective flock shaping recesses can advantageously suck larger amounts of air out of the flock box, through the bottoms of the shaping recesses which are not yet covered with and thus blocked by flock. In that way the excess air which has been branched away by way of the partial flow can be effectively and efficiently removed from the flock box and at the same time the flock contained in the partial flow in question can be used for producing the respective absorbent pad in the shaping recess.

In accordance with a preferred feature of the invention, the branching of the feed conduit can be such that it produces the first partial flow with a higher volume-specific proportion of flock than the second partial flow and correlatively the second partial flow has a lower volume-specific proportion of flock than the first partial flow. This can still further improve the level of efficiency in terms of removing the air from the apparatus in accordance with the invention. As the second partial flow is directed on to a location of the shaping recess carrier which, as considered in the direction of movement thereof, is substantially downstream of the region of impingement of the first partial flow on to the shaping recess carrier, the shaping recesses which freshly pass into the region of the shaping recess carrier which is covered by the flock box are in this case less rapidly filled with flock and their sieve-like bottoms enjoy a higher degree of permeability to the air, over a longer period of time. As indicated, that in turn permits the excess air to be sucked away in a more efficient manner.

It should be expressly mentioned that, in accordance with the present invention, the partial flows may entail the same volume-specific proportions of flock, as well as different proportions of flock.

In accordance with a further preferred feature of the invention it is possible for three or even more partial flows to be branched off the feed conduit which carries the flock-air mixture. In that situation, it is particularly advantageous for a third conduit to be so directed that the third partial flow carried therein meets the shaping recess carrier substantially upstream of the first partial flow, as considered in the direction of movement of the shaping recess carrier. The first partial flow then passes between the second and third partial flows and it is possible to add thereto a hydrophilic additive, usually a super absorbent polymer, usually referred to as SAP. That additive can be specifically introduced in that way into the region which will constitute the central layer of the absorbent pad in the finished condition. It is thereby securely held in position in the absorbent pad and cannot accidentally come loose from the flock bonding of the absorbent pad.

In order to break up and disperse compacted pieces of flock material or flock lumps within the flock-air mixtures constituting the partial flows, which can occur due to friction with the wall surfaces of the conduits, flow turbulence phenomena as well as static charging, the conduits carrying the partial flows may include pneumatic dispersing devices for dispersing the flock lumps, which are operative to break up and disperse the lumps by accelerating the flock-air mixture of the respective partial flow, together with the flock lumps contained therein, in such a way that the flock lumps are torn apart or burst asunder.

It was surprisingly found that flock lumps which comprise compacted cellulose flocks or fibers can be broken up and dispersed if they are accelerated suddenly with a jerk, jolt or jump by means of a directed flow of fluid, in particular an air flow, of high kinetic energy. In that situation, acceleration and/or fluid friction forces occur, which readily overcome the mechanical and/or electrostatic adhesion forces which are operative between the flocks forming a flock lump. Furthermore, the pneumatic dispersing device according to the invention preferably generates turbulent flows whose acceleration effects which change randomly in respect of direction and magnitude have the result that the flock lumps disintegrate. It has been found to be particularly advantageous in this respect for the flock-air mixture to be accelerated to supersonic speed, preferably to up to twice the speed of sound. Such high speeds ensure that turbulent flow conditions obtain in the dispersing device and the flock-air mixture constituting the respective partial flow is sufficiently accelerated in a jerk-like, jolt-like or jump fashion.

Depending on the respective magnitude of the forces which hold a flock lump together, dispersion of the flock lump occurs at an earlier or later time. A flock lump which is less firmly held together can already be torn apart at the beginning of the acceleration phase whereas a flock lump which is more firmly held together can under some circumstances be destroyed only after the attainment of an adequate degree of turbulence in the flow of the flock-air mixture. At any event the apparatus and the method according to the invention provide that, in contrast to impact arrangements which mechanically break up lumps by the latter impacting against for example fixed bars in a flow conduit, all flock lumps contained in the flock-air mixture flowing through the feed conduit are operatively engaged by the acceleration forces to cause appropriate disintegration and dispersion thereof.

In accordance with a preferred feature of the apparatus of the invention, the pneumatic dispersing device can be arranged in the end region of each of the conduits which carries the partial flows of the flock-air mixture. Preferably, the dispersing device is fitted directly into the opening of the respective conduit into the flock-laying device. The flock-laying device includes a rotating flock-shaping wheel and a stationary flock box into which at least one of the conduits opens by way of the pneumatic dispersing device. The directed jet of the substantially lump-free flock-air mixture which is produced by the pneumatic dispersing device means that it is advantageously possible for that jet to be directed specifically and targetedly in a given direction in space. This means that troughs or shaping recesses provided in the peripheral surface of the flock-shaping wheel, for forming the absorbent pads, can be more effectively filled with flock.

In accordance with another preferred feature of the invention the pneumatic dispersing device can be formed by a nozzle around which the flock-air mixture flows. The nozzle is arranged substantially in the central region of the cross-section of the conduit carrying the respective partial flow. With this configuration of the dispersing device it will be noted that it is necessary for the compressed air which is to be discharged from the nozzle under high pressure to be introduced into the central region of the cross-section of the conduit region. The consequence of this is that at least one suitable pneumatic line must be passed into the central region of the cross-section of the conduit, which means that the at least one pneumatic line is in the flow path of the flock-air mixture and thus, in addition to the pneumatic action of dispersing the flock lumps, can also afford a mechanical dispersing action in the same manner as previous dispersing device involving impact bars against which the flock-air mixture impinges to cause lumps to be dispersed.

In a further preferred feature the pneumatic dispersing device is in the form of an injector nozzle in the form of a tube portion, with the flock-air mixture constituting the respective partial flow flowing through the injector nozzle itself. A pressure fluid under high pressure, more particularly for example compressed air, is fed to the injector nozzle by way of one and preferably a plurality of flow openings which are in the form of feed passages. The pressure fluid can either come from a pressure fluid source which is additionally provided for that purpose, or it can come from a pressure fluid source which in any case is already present for other systems of the machines involved in the present context. The preferably plurality of feed passages in accordance with the invention can be disposed in the outer peripheral region of the flow space of the injector nozzle, through which the flock-air mixture flows.

It will be appreciated that the pneumatic dispersing device or injector nozzle acts in a fluid-mechanics fashion like a fluid or air flow booster. A reduced pressure obtains at the entry or intake side while an increased pressure occurs at the exit or ejection side thereof. The dispersing device or injector nozzle can therefore act like a suction blower arranged at the end of the conduit carrying the respective partial flow of the flock-air mixture, so that, depending on the respective overall length of the conduits, it is possible to forego the inclusion of a further fan or blower in the flock-delivery path.

Further objects, features and advantages of the invention will be apparent from the description hereinafter of a preferred embodiment of the invention.

BRIEF DESCRIPTION OF THE DRAWING

FIG. 1 is a diagrammatic side view of an apparatus according to the invention for the production of absorbent pads from a flock-air mixture, FIG. 2 is a diagrammatic view showing a pneumatic dispersing device in the form of an injector nozzle, FIG. 3 is a view of the injector nozzle of FIG. 2 from above, and FIG. 4 is a view in section on line A—A in FIG. 3.

DESCRIPTION OF THE PREFERRED EMBODIMENT

Referring firstly to FIG. 1, shown therein is an apparatus according to the invention for producing absorbent pads 2 from a flock-air mixture. The absorbent pads 2 can be a constituent of sanitary napkins, disposable diapers, or similar hygiene articles. A crushing device or disintegrating device 3 is supplied from a supply roll 5 with a cardboard or cellulose web 6. The web 6 is broken up into cellulose flocks or pulp in the disintegrating device 3. Alternatively, the cellulose flocks could also be made available in some other fashion, for example they may already be available in the form of ready cellulose flocks. Those flocks are mixed with carrier air and are transported in the form of a flock-air mixture through a feed conduit 7 to a flock-laying device indicated generally by reference 4. Depending on the respective length of the feed conduit 7, the assembly may include a fan or blower 8 for supporting the flow of carrier air in the course of the feed conduit 7.

The flock-laying device 4 substantially includes a flock-shaping wheel 10 and a hollow flock box 9 which covers over the flock-shaping wheel 10 in a predetermined peripheral region thereof and is open there to the flock-shaping wheel 10. The flock-shaping wheel 10 rotates in the counterclockwise direction as indicated by the arrow 15. In its peripheral casing or in its outer peripheral region the flock-shaping wheel 10 has troughs or shaping recesses 11 which are provided with sieve-like bottoms 12. A suction box 13 which is stationary, that is to say which does not therefore rotate with the flock-shaping wheel 10, makes it possible for flock-air mixture to be sucked into the shaping recesses 11 through the sieve-like bottoms 12, in that peripheral region of the flock-shaping wheel 10 which is covered over by the flock box 9. As a result, the desired flock cores or absorbent pads 2 are formed in those shaping recesses 11 which are in the region which is covered over by the flock box 9.

Arranged at an upstream position in relation to the flock-shaping wheel 10 in the direction of rotation as indicated by the arrow 15 is a brushing-off device 16 which removes the flock material projecting beyond the outer peripheral surface from the shaping recesses 11, and which feeds the removed flock material back to the disintegrating device 3 by way of a return conduit (not shown). Then, the absorbent pads which have been brushed flush with the peripheral surface of the wheel 10 in that way are removed from the shaping recesses 11 by means of a suction roller 17 and placed on a conveyor belt 18 which feeds them to a machine (not shown) for the production of sanitary napkins, panty liners, diapers or the like.

As can be seen from FIG. 1 the feed conduit 7 branches just downstream of the fan 8 at a first branching location which is clearly shown in FIG. 1 but not referenced. At that branching location, there is a first conduit 7' which operates in effect as a main flow conduit insofar as it constitutes a continuation of the feed conduit 7, and a second conduit 7Δ which operates as a secondary flow conduit branching from the first conduit 7'. The second conduit 7" extends arcuately and opens inclinedly from above into the flock box indicated at 9. As the first partial flow of flock-air mixture which flows through the conduit 7' is not changed in its direction of flow at the first branching location, in the illustrated embodiment it involves a higher volume-specific proportion of flock than the second partial flow which flows through the conduit 7" and which conveys substantially excess support air into the flock box 9. By varying the geometry of the first branching location and the way in which the flock-air mixture is guided there as well as the cross-sectional ratio as between the first conduit 7' and the second conduit 7", it is possible to adjust the desired ratios of the first partial flow to the second partial flow and the respective flock proportions thereof. For example it is possible to provide a valve at the first branching location, whereby the second conduit 7" or the first conduit 7' can be closed off if required.

The direction in which the second conduit 7" opens into the flock box 9 was so selected that the second partial flow is guided into that region of the flock box 9 into which shaping recesses 11 which are still unfilled pass in the direction of rotation as indicated by the arrow 15 of the flock-shaping wheel 10. Reference numeral 13 denotes a suction box which can thus suck away the excess air in the form of the second partial flow without involving a high level of flow resistance through the sieve-like bottoms 12 of the shaping recesses 11.

The main flow of the flock-air mixture passes through the first conduit 7' by way of a pneumatic dispersing device 20 for breaking up and dispersing lumps of flock into the flock box 9. The dispersing box 20 which produces a directed air jet is so oriented in this arrangement that the main flow, as considered in the direction of rotation indicated by the arrow 15, encounters the flock-shaping wheel 10 upstream of the secondary flow issuing from the conduit 7".

Disposed downstream of the first branching location is a second branching location at which the main flow conduit or the first conduit 7' branches to afford a third conduit 7'". The third conduit 7'" extends beneath the conduit 7' as can be clearly seen from FIG. 1 and also opens below the conduit 7' into the flock box 9. A further pneumatic dispersing device which is shown in FIG. 1 but not identified but which is of a corresponding configuration to the first-mentioned dispersing device 20 is also provided in the mouth region of the conduit 7'" where it opens into the flock box 9, in order to break up and disperse flock lumps in the flow through the conduit 7'". It will be seen that the third partial flow is deflected at the second branching location, in contrast to the main flow which continues on through the conduit 7', so that in the illustrated embodiment the third partial flow contains a smaller volume-specific proportion of flock than the main flow in the conduit 7'. If necessary, a valve can also be provided at the abovementioned second branching location for closing off the first conduit 7' or the third conduit 7'".

Provided downstream of the second branching location on the first conduit 7' is a connecting portion 21 for connecting a supply conduit (not shown) for feeding a hydrophilic additive thereto. The hydrophilic additive is for example a super absorbent polymer, referred to as SAP. By virtue of the feed conduit 7 branching into the first, second and third conduits 7', 7" and 7''', the SAP can be cleverly and specifically bound into the central layer of the finished absorbent pad 2. That is achieved by the empty shaping recesses 11 which in the direction of rotation indicated by the arrow 15 pass into the region in which the flock box 9 and the flock-shaping wheel 10 overlap firstly being filled with flock by means of the second partial flow from the second conduit 7". A first layer of the absorbent pad 2 is accordingly formed on the sieve-like bottoms of the respective shaping recesses 11. With increasing rotary movement of the flock-shaping wheel 10, the shaping recess 11 in question increasingly approaches the first partial flow which is issuing from the first conduit 7' and which is composed of the mixture made up of flock, air and SAP. A further second layer of the absorbent pad 2 is formed from that mixture in the shaping recess 11. Further rotary movement of the flock-shaping wheel 10 in the direction of rotation 15 causes the shaping recess 11 in question to approach that location at which the third partial flow is directed on to the flock-shaping wheel 10 from the third conduit 7'''. As the third partial flow does not contain any SAP, that results in the formation in the shaping recess 11 of a third layer of the absorbent pad 2 which does not contain any additive, like the layer which was first formed.

The hydrophilic additive such as SAP is in that way so-to-speak wrapped or enveloped in the absorbent pad 2, thereby ensuring that the SAP cannot readily come away from the absorbent pad 2 and come into contact with mucous membranes.

Figure 2:
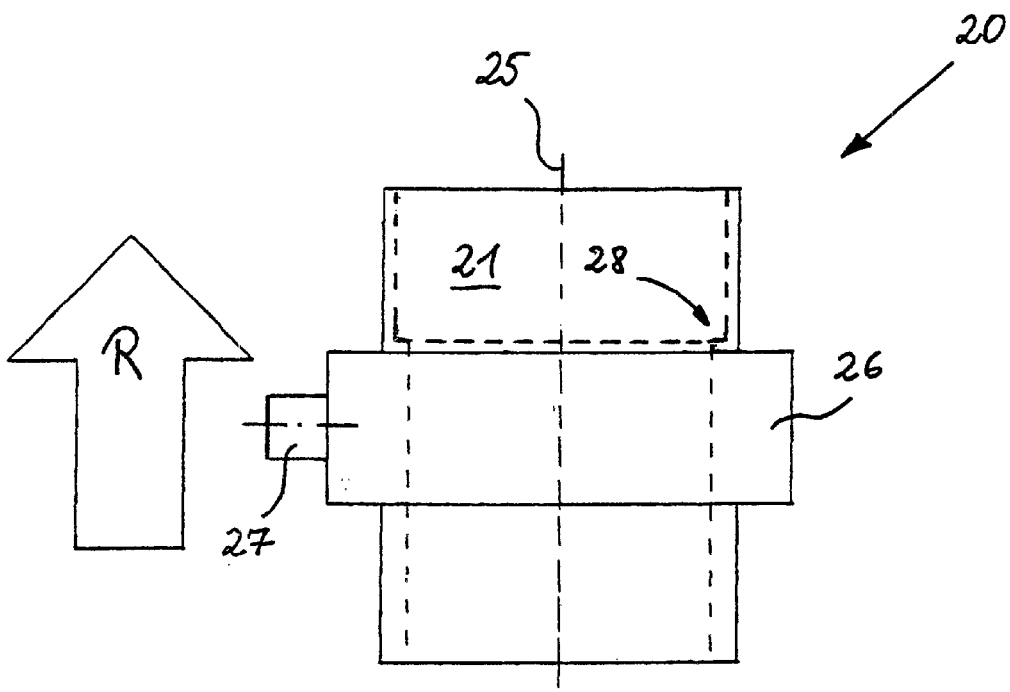
Figure 3:
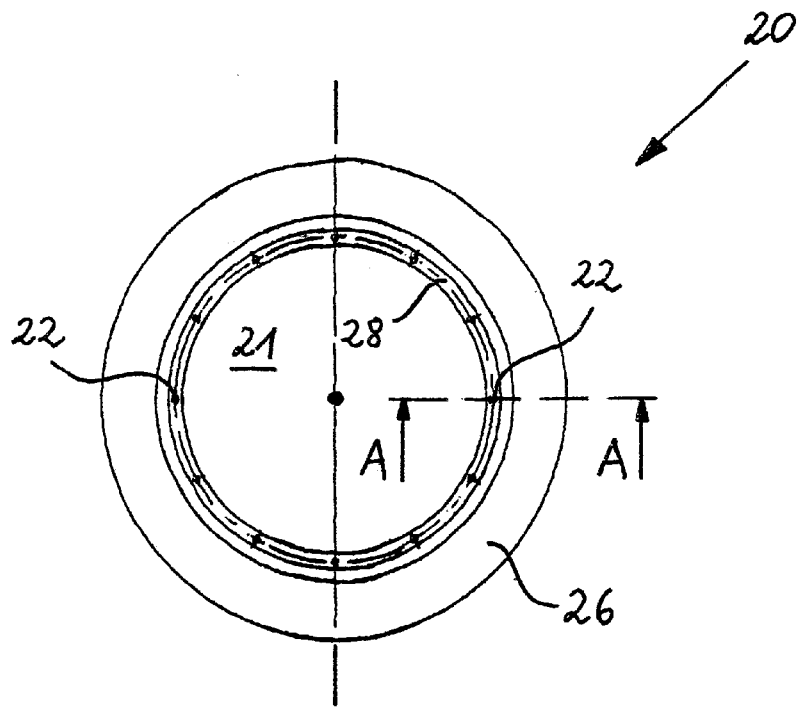

Reference will now be made to FIGS. 2 and 3 showing an injector nozzle 20 which functions as the pneumatic dispersing device. The injector nozzle 20 comprises a comparatively short tube portion which is fitted into the downstream end part of the respective conduits 7' and 7'''. In the illustrated embodiment, the second conduit 7" opens without an injector nozzle into the flock box 9 as the proportion of flock in the second partial flow which passes through the second conduit 7" is so small that the formation of flock lumps worth mentioning in the conduit 7" is not something to be seriously feared. In its region which is the central region in its longitudinal direction, the injector nozzle 20 has a bead or ridge 26 in which there is formed an annular passage 23 which extends completely around the tube portion, as can be seen from the sectional view in FIG. 4. The annular passage 23 is in flow communication by way of the connection portion 27 with a pneumatic fluid or compressed air source (not shown) which can be provided specifically for the injector nozzle 20 or which is already present for use by other systems of the respective machine.

In the view shown in FIG. 2, the flock-air mixture flows upwardly through the injector nozzle 20 as indicated by the arrow R. In doing so, it flows in particular through the flow space indicated at 21 in the interior of the injector nozzle 20, the flow space 21 being of a cylindrical cross-section in the illustrated embodiment. Alternatively however, it may also be of a cross-section which increases in the flow direction R and thereby act as a diffuser. As can be clearly seen from FIGS. 2 and 3 the flow space 21 is of a larger inside diameter than the remaining space, which is shown therebeneath in FIG. 2, in the interior of the injector nozzle 20. That design configuration affords a step 28 in the form of a circular ring at the level of the lower plane defining the flow space 21, as is shown in the plan view of FIG. 3.

Figure 4:
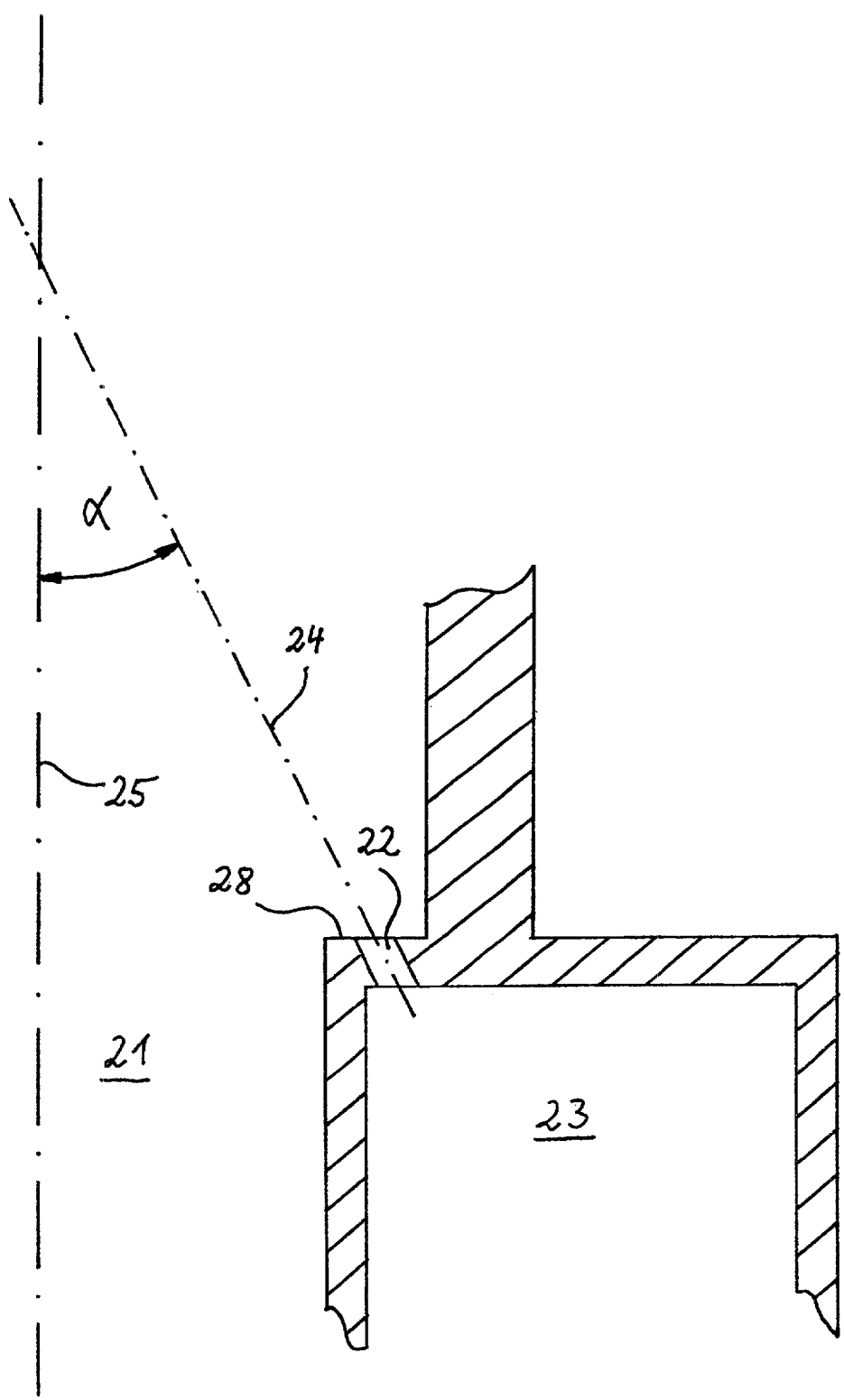

As can best be seen from FIGS. 3 and 4, a total of twelve feed passages 22 which act as feed openings open into the annular surface of the step 28 in the illustrated embodiment. The feed passages 22 are distributed at uniform angular spacings over the peripheral extent of the step 28. Alternatively however it is also possible to provide more than or fewer than twelve feed passages, or to arrange the feed passages at nonuniform angular spacings in order if necessary to produce specific flow profiles over the cross-section of the injector nozzle 20.

As shown in FIG. 4, the feed passages 22 are in flow communication with the annular passage 23 and therefore also with the compressed air source which is connected to the connecting portion indicated at 27 in FIG. 2.

Looking still at FIG. 4, the axis as indicated at 24 of the feed passage 22 shown therein is inclined at the angle of inclination a with respect to the longitudinal axis or axis of symmetry as indicated at 25 of the injector nozzle 20. The longitudinal axis is also indicated at 25 in FIG. 2. That configuration provides that the compressed air is supplied not just axially in the flow direction indicated at R in FIG. 2, but also with a velocity component which is directed radially inwardly towards the longitudinal axis 25. That action, in addition to the acceleration forces which break up and disperse the flock lumps, can also produce a further effect which promotes dispersion of the flock lumps and which provides that the flock lumps present are blown radially inwardly out of the radially outer regions of the cross-section of the jet of flock-air mixture and are thereby caused under some circumstances to collide with each other whereby they are torn apart or broken up. In accordance with the invention the angle of inclination $\alpha$ can be 50° or less, with the inequality $5° \leqq \alpha \leqq 30°$ preferably applying. Alternatively the angle $\alpha$ can also be 0°, which therefore means that the axis 24 of the feed passages 22 extends parallel to the longitudinal axis 25 of the injector nozzle 20.

Instead of a plurality of feed openings 22 in the form of bored passages, it is also possible to provide a single feed opening in the form of a peripherally extending passage in the nature of an annular gap, between the annular passage 23 and the flow space 21. With that structure, a larger cross-sectional area is available to the compressed air to be supplied, for it to flow into the flow space 21, so that a larger and spatially better distributed volume flow of compressed air can be fed to the flow space 21 and it is in that way possible to achieve a higher degree of effectiveness in terms of dispersing the flock lumps in the flock-air mixture.

It will be appreciated that the above-described apparatus for producing absorbent pads and the related method have been set forth solely by way of example and illustration of the principles of the invention and that various other modifications and alterations may be made therein without thereby departing from the spirit and scope of the invention.

What is claimed is:

1. An apparatus for producing absorbent pads from a flock-air mixture including:

a shaping recess carrier carrying recesses for forming the respective absorbent pads;

means for displacing the shaping recess carrier in a direction of operation; and a feed conduit for feeding the flock-air mixture to the shaping recess carrier, the feed conduit including a branching affording at least a first conduit, a second conduit, and a third conduit, the first conduit being operable to carry a first partial flow of the flock-air mixture, the second conduit being operable to carry a second partial flow of the flock-air mixture, and the third conduit being operable to carry a third partial flow of the flock-air mixture, the first and second conduits being directed to the shaping depression carrier at locations such that the second partial flow through the second conduit meets the shaping recess carrier substantially downstream of the first partial flow through the first conduit in the direction of operation of the shaping recess carrier;

wherein the third conduit is so directed that the third partial flow meets the shaping recess carrier substantially upstream of the first partial flow in the direction of operation of the shaping recess carrier, and further including means for feeding a hydrophilic additive to said first partial flow in a position such that said additive comes to lie substantially in a central layer of the absorbent pad, said branching being such that the first partial flow has a higher volume-specific proportion of flock than the second and third partial flows.

2. An apparatus for producing absorbent pads from a flock-air mixture including a shaping recess carrier carrying recesses for forming the respective absorbent pads;

means for displacing the shaping recess carrier in a direction of operation; and a feed conduit for feeding the flock-air mixture to the shaping recess carrier, the feed conduit including a branching affording at least a first and a second conduit, the first conduit being operable to carry a first partial flow of the flock-air mixture and the second conduit being operable to carry a second partial flow of the flock-air mixture, the first and second conduits being directed to the shaping depression carrier at locations such that the second partial flow through the second conduit meets the shaping recess carrier substantially downstream of the first partial flow through the first conduit in the direction of operation of the shaping recess carrier;

in at least one of said conduits a pneumatic dispersing device for dispersing flock lumps within the respective partial flow in the respective conduit, the dispersing device being operable to disperse the flock lumps by accelerating the flock-air mixture of the respective partial flow together with the lumps contained therein to cause the lumps to be broken up;

wherein the dispersing device includes a nozzle having at least one nozzle passage and arranged substantially in the central region of the cross-section of the at least one conduit and so positioned that the flock-air mixture in operation of the apparatus flows therearound;

and further including means for feeding pressure fluid from a pressure fluid source to the nozzle passage to accelerate the flock lumps.

3. An apparatus for producing absorbent pads from a flock-air mixture including a shaping recess carrier carrying recesses for forming the respective absorbent pads;

means for displacing the shaping recess carrier in a direction of operation; and a feed conduit for feeding the flock-air mixture to the shaping recess carrier, the feed conduit including a branching affording at least a first and a second conduit, the first conduit being operable to carry a first partial flow of the flock-air mixture and the second conduit being operable to carry a second partial flow of the flock-air mixture, the first and second conduits being directed to the shaping depression carrier at locations such that the second partial flow through the second conduit meets the shaping recess carrier substantially downstream of the first partial flow through the first conduit in the direction of operation of the shaping recess carrier;

in at least one of said conduits a pneumatic dispersing device for dispersing flock lumps within the respective partial flow in the respective conduit, the dispersing device being operable to disperse the flock lumps by accelerating the flock-air mixture of the respective partial flow together with the lumps contained therein to cause the lumps to be broken up;

wherein the dispersing device comprises an injector nozzle in the form of a tube portion and having a flow space for the flow therethrough of the flock-air mixture of the respective partial flow, the flow space including an outer peripheral region and comprising at least one feed opening in the outer peripheral region of the flow space for a feed therethrough to the flow space of pressure fluid for accelerating the flock lumps from a source of pressure fluid.

4. Apparatus as set forth in claim 3 and including an annular passage in flow communication with the at least one feed opening for supply with the pressure fluid.

5. Apparatus as set forth in claim 3 and including a plurality of feed openings in the form of feed passages arranged at uniform angular spacings in the outer peripheral region of the flow space.

6. Apparatus as set forth in claim 3 wherein the injector nozzle has a longitudinal axis and the axis of the at least one feed opening extends in parallel relationship with the longitudinal axis of the injector nozzle, the arrangement being such that the pressure fluid is fed to the flow space substantially axially in the flow direction of the flock-air mixture of the respective partial flow in the respective conduit.

7. Apparatus as set forth in claim 3 wherein the injector nozzle has a longitudinal axis and the axis of the at least one feed opening is inclined at an angle with respect to the longitudinal axis of the injector nozzle, the arrangement being such that the pressure fluid is fed to the flow space both with an axial and with a radial flow component.

8. Apparatus as set forth in claim 7 wherein the inequality $0 \leq \alpha \leq 50°$ applies for the angle of inclination.

9. Apparatus as set forth in claim 8 wherein the inequality $5 \leq \alpha \leq 30°$ applies for the angle of inclination.

* * * * *